(12) United States Patent
Chojin

(10) Patent No.: US 8,016,827 B2
(45) Date of Patent: Sep. 13, 2011

(54) APPARATUS, SYSTEM, AND METHOD FOR PERFORMING AN ELECTROSURGICAL PROCEDURE

(75) Inventor: Edward M. Chojin, Boulder, CO (US)

(73) Assignee: TYCO Healthcare Group LP, Boulder, CO (US)

( * ) Notice: Subject to any disclaimer, the term of this patent is extended or adjusted under 35 U.S.C. 154(b) by 532 days.

(21) Appl. No.: 12/248,104

(22) Filed: Oct. 9, 2008

(65) Prior Publication Data

US 2010/0094286 A1 Apr. 15, 2010

(51) Int. Cl.
*A61B 18/18* (2006.01)

(52) U.S. Cl. .......................................... 606/51

(58) Field of Classification Search .............. 606/49, 606/50, 51, 52, 205, 206, 207, 208, 209
See application file for complete search history.

(56) References Cited

U.S. PATENT DOCUMENTS

| | | | |
|---|---|---|---|
| 371,664 | A | 10/1887 | Brannan et al. |
| 702,472 | A | 6/1902 | Pignolet |
| 728,883 | A | 5/1903 | Downes |
| 1,586,645 | A | 6/1926 | Bierman |
| 1,813,902 | A | 7/1931 | Bovie |
| 1,822,330 | A | 9/1931 | Ainslie |
| 1,852,542 | A | 4/1932 | Sovatkin |
| 2,002,594 | A | 5/1935 | Wappler et al. |
| 2,011,169 | A | 8/1935 | Wappler |
| 2,031,682 | A | 2/1936 | Wappler et al. |
| 2,054,149 | A | 9/1936 | Wappler |
| 2,176,479 | A | 10/1939 | Willis |
| 2,305,156 | A | 4/1941 | Grubel |
| 2,245,030 | A * | 6/1941 | Gottesfeld et al. ............... 251/7 |
| 2,279,753 | A | 4/1942 | Knopp |
| 2,327,353 | A | 8/1943 | Karle |
| 2,632,661 | A | 8/1948 | Cristofv |
| 2,668,538 | A | 2/1954 | Baker |
| 2,796,065 | A | 6/1957 | Kapp |
| 3,073,311 | A | 1/1963 | Tibbs et al. |

(Continued)

FOREIGN PATENT DOCUMENTS

CA 2104423 2/1994

(Continued)

OTHER PUBLICATIONS

Michael Choti, "Abdominoperineal Resection with the LigaSure Vessel Sealing System and LigaSure Atlas 20 cm Open Instrument" ; Innovations That Work, Jun. 2003.

(Continued)

*Primary Examiner* — Theodore Stigell
*Assistant Examiner* — William Carpenter

(57) ABSTRACT

A bipolar forceps includes a housing having a shaft extending therefrom including an end effector assembly at a distal end thereof. The end effector assembly has a wheel assembly opposing a jaw member and having a pair of opposing wheels configured to facilitate movement of the wheel assembly relative to the jaw member. A drive rod is operably coupled at a proximal end to a movable handle and at a distal end to the wheel assembly. The movable handle is movable relative to a stationary handle to move the wheel assembly relative to the jaw member. At least one electrically conductive tissue sealing plate is disposed on each of the wheel assembly and the jaw member and is adapted to connect to an electrosurgical energy source configured to deliver electrosurgical energy to tissue held between the wheel assembly and the jaw member to effect a tissue seal.

15 Claims, 4 Drawing Sheets

U.S. PATENT DOCUMENTS

| | | |
|---|---|---|
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,397,325 A * | 3/1995 | Della Badia et al. ......... 606/144 |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |

| Patent No. | Date | Inventor(s) |
|---|---|---|
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,512,721 A | 4/1996 | Young et al. |
| 5,514,134 A | 5/1996 | Rydell et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,646 A | 7/1998 | Koblish et al. |
| 5,779,701 A | 7/1998 | McBrayer et al. |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,093 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |

| | | | | | | |
|---|---|---|---|---|---|---|
| 5,827,279 | A | 10/1998 | Hughett et al. | 6,099,550 | A | 8/2000 | Yoon |
| 5,827,281 | A | 10/1998 | Levin | 6,102,909 | A | 8/2000 | Chen et al. |
| 5,827,323 | A | 10/1998 | Klieman et al. | 6,106,542 | A | 8/2000 | Toybin et al. |
| 5,827,548 | A | 10/1998 | Lavallee et al. | 6,110,171 | A | 8/2000 | Rydell |
| 5,833,690 | A | 11/1998 | Yates et al. | 6,113,596 | A | 9/2000 | Hooven et al. |
| 5,843,080 | A | 12/1998 | Fleenor et al. | 6,113,598 | A | 9/2000 | Baker |
| 5,849,022 | A | 12/1998 | Sakashita et al. | 6,117,158 | A | 9/2000 | Measamer et al. |
| 5,853,412 | A | 12/1998 | Mayenberger | 6,122,549 | A | 9/2000 | Sharkey et al. |
| 5,859,527 | A | 1/1999 | Cook | 6,123,701 | A | 9/2000 | Nezhat |
| 5,860,976 | A | 1/1999 | Billings et al. | H1904 | H | 10/2000 | Yates et al. |
| 5,876,401 | A | 3/1999 | Schulze et al. | 6,126,658 | A | 10/2000 | Baker |
| 5,876,412 | A | 3/1999 | Piraka | 6,126,665 | A | 10/2000 | Yoon |
| 5,882,567 | A | 3/1999 | Cavallaro et al. | 6,139,563 | A | 10/2000 | Cosgrove, III et al. |
| 5,891,141 | A | 4/1999 | Rydell | 6,143,005 | A | 11/2000 | Yoon et al. |
| 5,891,142 | A | 4/1999 | Eggers et al. | 6,152,923 | A | 11/2000 | Ryan |
| 5,893,863 | A | 4/1999 | Yoon | 6,162,220 | A | 12/2000 | Nezhat |
| 5,893,875 | A | 4/1999 | O'Connor et al. | 6,171,316 | B1 | 1/2001 | Kovac et al. |
| 5,893,877 | A | 4/1999 | Gampp, Jr. et al. | 6,174,309 | B1 | 1/2001 | Wrublewski et al. |
| 5,897,563 | A | 4/1999 | Yoon et al. | 6,178,628 | B1 | 1/2001 | Clemens et al. |
| 5,902,301 | A | 5/1999 | Olig | 6,179,834 | B1 | 1/2001 | Buysse et al. |
| 5,906,630 | A | 5/1999 | Anderhub et al. | 6,179,837 | B1 | 1/2001 | Hooven |
| 5,908,420 | A | 6/1999 | Parins et al. | 6,183,467 | B1 | 2/2001 | Shapeton et al. |
| 5,908,432 | A | 6/1999 | Pan | 6,187,003 | B1 | 2/2001 | Buysse et al. |
| 5,911,719 | A | 6/1999 | Eggers | 6,190,386 | B1 | 2/2001 | Rydell |
| 5,913,874 | A | 6/1999 | Berns et al. | 6,190,400 | B1 | 2/2001 | Vandemoer et al. |
| 5,921,916 | A | 7/1999 | Aeikens et al. | 6,193,718 | B1 | 2/2001 | Kortenbach et al. |
| 5,921,984 | A | 7/1999 | Sutcu et al. | 6,206,876 | B1 | 3/2001 | Levine et al. |
| 5,925,043 | A | 7/1999 | Kumar et al. | 6,206,877 | B1 | 3/2001 | Kese et al. |
| 5,928,136 | A | 7/1999 | Barry | 6,206,893 | B1 | 3/2001 | Klein et al. |
| 5,935,126 | A | 8/1999 | Riza | 6,214,028 | B1 | 4/2001 | Yoon et al. |
| 5,941,869 | A | 8/1999 | Patterson et al. | 6,217,602 | B1 | 4/2001 | Redmon |
| 5,944,718 | A | 8/1999 | Austin et al. | 6,217,615 | B1 | 4/2001 | Sioshansi et al. |
| 5,951,546 | A | 9/1999 | Lorentzen | 6,221,039 | B1 | 4/2001 | Durgin et al. |
| 5,951,549 | A | 9/1999 | Richardson et al. | 6,223,100 | B1 | 4/2001 | Green |
| 5,954,720 | A | 9/1999 | Wilson et al. | 6,224,593 | B1 | 5/2001 | Ryan et al. |
| 5,954,731 | A | 9/1999 | Yoon | 6,224,614 | B1 | 5/2001 | Yoon |
| 5,954,733 | A | 9/1999 | Yoon | 6,228,080 | B1 | 5/2001 | Gines |
| 5,957,923 | A | 9/1999 | Hahnen et al. | 6,228,083 | B1 | 5/2001 | Lands et al. |
| 5,957,937 | A | 9/1999 | Yoon | 6,248,124 | B1 | 6/2001 | Pedros et al. |
| 5,960,544 | A | 10/1999 | Beyers | 6,248,944 | B1 | 6/2001 | Ito |
| 5,961,514 | A | 10/1999 | Long et al. | 6,261,307 | B1 | 7/2001 | Yoon et al. |
| 5,964,758 | A | 10/1999 | Dresden | 6,267,761 | B1 | 7/2001 | Ryan |
| 5,976,132 | A | 11/1999 | Morris | 6,270,497 | B1 | 8/2001 | Sekino et al. |
| 5,984,932 | A | 11/1999 | Yoon | 6,270,508 | B1 * | 8/2001 | Klieman et al. ............... 606/147 |
| 5,984,938 | A | 11/1999 | Yoon | 6,273,887 | B1 | 8/2001 | Yamauchi et al. |
| 5,984,939 | A | 11/1999 | Yoon | 6,277,117 | B1 | 8/2001 | Tetzlaff et al. |
| 5,989,277 | A | 11/1999 | LeMaire, III et al. | 6,280,458 | B1 | 8/2001 | Boche et al. |
| 5,993,466 | A | 11/1999 | Yoon | 6,283,961 | B1 | 9/2001 | Underwood et al. |
| 5,993,467 | A | 11/1999 | Yoon | D449,886 | S | 10/2001 | Tetzlaff et al. |
| 5,997,565 | A | 12/1999 | Inoue | 6,298,550 | B1 | 10/2001 | Kirwan |
| 6,004,332 | A | 12/1999 | Yoon et al. | 6,302,424 | B1 | 10/2001 | Gisinger et al. |
| 6,004,335 | A | 12/1999 | Vaitekunas et al. | 6,319,262 | B1 | 11/2001 | Bates et al. |
| 6,010,516 | A | 1/2000 | Hulka | 6,319,451 | B1 | 11/2001 | Brune |
| 6,017,358 | A | 1/2000 | Yoon et al. | 6,322,561 | B1 | 11/2001 | Eggers et al. |
| 6,021,693 | A | 2/2000 | Feng-Sing | 6,322,580 | B1 | 11/2001 | Kanner |
| 6,024,741 | A | 2/2000 | Williamson et al. | 6,325,795 | B1 | 12/2001 | Lindemann et al. |
| 6,024,743 | A | 2/2000 | Edwards | 6,334,860 | B1 | 1/2002 | Dorn |
| 6,024,744 | A | 2/2000 | Kese et al. | 6,334,861 | B1 | 1/2002 | Chandler et al. |
| 6,027,522 | A | 2/2000 | Palmer | 6,345,532 | B1 | 2/2002 | Coudray et al. |
| 6,030,384 | A | 2/2000 | Nezhat | 6,350,264 | B1 | 2/2002 | Hooven |
| 6,033,399 | A | 3/2000 | Gines | 6,352,536 | B1 | 3/2002 | Buysse et al. |
| 6,039,733 | A | 3/2000 | Buysse et al. | 6,358,249 | B1 | 3/2002 | Chen et al. |
| 6,041,679 | A | 3/2000 | Slater et al. | 6,358,259 | B1 | 3/2002 | Swain et al. |
| 6,050,996 | A | 4/2000 | Schmaltz et al. | 6,358,268 | B1 | 3/2002 | Hunt et al. |
| 6,053,914 | A | 4/2000 | Eggers et al. | 6,364,879 | B1 | 4/2002 | Chen et al. |
| 6,053,933 | A | 4/2000 | Balazs et al. | D457,958 | S | 5/2002 | Dycus et al. |
| D424,694 | S | 5/2000 | Tetzlaff et al. | D457,959 | S | 5/2002 | Tetzlaff et al. |
| D425,201 | S | 5/2000 | Tetzlaff et al. | 6,387,094 | B1 | 5/2002 | Eitenmuller |
| 6,059,782 | A | 5/2000 | Novak et al. | 6,391,035 | B1 | 5/2002 | Appleby et al. |
| 6,066,139 | A | 5/2000 | Ryan et al. | 6,398,779 | B1 | 6/2002 | Buysse et al. |
| 6,074,386 | A | 6/2000 | Goble et al. | 6,402,747 | B1 | 6/2002 | Lindemann et al. |
| 6,077,287 | A | 6/2000 | Taylor et al. | 6,409,728 | B1 | 6/2002 | Ehr et al. |
| 6,080,180 | A | 6/2000 | Yoon et al. | H2037 | H | 7/2002 | Yates et al. |
| RE36,795 | E | 7/2000 | Rydell | 6,419,675 | B1 | 7/2002 | Gallo, Sr. |
| 6,083,223 | A | 7/2000 | Baker | 6,425,896 | B1 | 7/2002 | Baltschun et al. |
| 6,086,586 | A | 7/2000 | Hooven | 6,432,112 | B2 | 8/2002 | Brock et al. |
| 6,086,601 | A | 7/2000 | Yoon | 6,440,144 | B1 | 8/2002 | Bacher |
| 6,090,107 | A | 7/2000 | Borgmeier et al. | 6,443,952 | B1 | 9/2002 | Mulier et al. |
| 6,096,037 | A | 8/2000 | Mulier et al. | 6,443,970 | B1 | 9/2002 | Schulze et al. |

| | | |
|---|---|---|
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,536 B2 * | 2/2003 | Hooven et al. .................. 606/41 |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Pedersen et al. |
| 6,554,844 B2 * | 4/2003 | Lee et al. ...................... 606/130 |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Lands et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 * | 12/2003 | Bacher et al. .................... 606/51 |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |

| | | | | | | |
|---|---|---|---|---|---|---|
| 7,156,846 B2 | 1/2007 | Dycus et al. | | 2003/0158549 A1 | 8/2003 | Swanson |
| 7,160,298 B2 | 1/2007 | Lawes et al. | | 2003/0171747 A1 | 9/2003 | Kanehira et al. |
| 7,160,299 B2 | 1/2007 | Baily | | 2003/0181910 A1 | 9/2003 | Dycus et al. |
| 7,169,146 B2 | 1/2007 | Truckai et al. | | 2003/0216732 A1 | 11/2003 | Truckai et al. |
| 7,179,255 B2 | 2/2007 | Lettice et al. | | 2003/0220637 A1 | 11/2003 | Truckai et al. |
| 7,179,258 B2 | 2/2007 | Buysse et al. | | 2003/0229344 A1 | 12/2003 | Dycus et al. |
| 7,195,631 B2 | 3/2007 | Dumbauld | | 2003/0236325 A1 | 12/2003 | Bonora |
| D541,418 S | 4/2007 | Schechter et al. | | 2003/0236518 A1 | 12/2003 | Marchitto et al. |
| 7,207,990 B2 | 4/2007 | Lands et al. | | 2004/0030330 A1 | 2/2004 | Brassell et al. |
| D541,938 S | 5/2007 | Kerr et al | | 2004/0030332 A1 | 2/2004 | Knowlton et al. |
| 7,223,264 B2 | 5/2007 | Daniel et al. | | 2004/0049185 A1 | 3/2004 | Latterell et al. |
| 7,223,265 B2 | 5/2007 | Keppel | | 2004/0064151 A1 | 4/2004 | Mollenauer |
| 7,232,440 B2 | 6/2007 | Dumbauld et al. | | 2004/0073238 A1 | 4/2004 | Makower |
| 7,241,288 B2 | 7/2007 | Braun | | 2004/0073256 A1 | 4/2004 | Marchitto et al. |
| 7,241,296 B2 | 7/2007 | Buysse et al. | | 2004/0078035 A1 | 4/2004 | Kanehira et al. |
| 7,244,257 B2 | 7/2007 | Podhajsky et al. | | 2004/0082952 A1 | 4/2004 | Dycus et al. |
| 7,246,734 B2 | 7/2007 | Shelto, IV | | 2004/0087943 A1 | 5/2004 | Dycus et al. |
| 7,248,944 B2 | 7/2007 | Green | | 2004/0115296 A1 | 6/2004 | Duffin |
| 7,252,667 B2 | 8/2007 | Moses et al. | | 2004/0116924 A1 | 6/2004 | Dycus et al. |
| 7,255,697 B2 * | 8/2007 | Dycus et al. ............... 606/49 | | 2004/0116979 A1 | 6/2004 | Truckai et al. |
| 7,267,677 B2 | 9/2007 | Johnson et al. | | 2004/0143263 A1 | 7/2004 | Schechter et al. |
| 7,270,660 B2 | 9/2007 | Ryan | | 2004/0148035 A1 | 7/2004 | Barrett et al. |
| 7,270,664 B2 | 9/2007 | Johnson et al. | | 2004/0162557 A1 | 8/2004 | Tetzlaff et al. |
| 7,276,068 B2 | 10/2007 | Johnson et al. | | 2004/0193153 A1 | 9/2004 | Sartor et al. |
| 7,300,435 B2 | 11/2007 | Wham et al. | | 2004/0199181 A1 | 10/2004 | Knodel et al. |
| 7,303,557 B2 | 12/2007 | Wham et al. | | 2004/0210282 A1 | 10/2004 | Flock et al. |
| 7,311,709 B2 | 12/2007 | Truckai et al. | | 2004/0224590 A1 | 11/2004 | Rawa et al. |
| 7,314,471 B2 | 1/2008 | Holman | | 2004/0230189 A1 | 11/2004 | Keppel |
| 7,318,823 B2 | 1/2008 | Sharps et al. | | 2004/0236326 A1 | 11/2004 | Schulze et al. |
| 7,329,256 B2 | 2/2008 | Johnson et al. | | 2004/0243125 A1 | 12/2004 | Dycus et al. |
| 7,329,257 B2 | 2/2008 | Kanehira et al. | | 2004/0249374 A1 | 12/2004 | Tetzlaff et al. |
| D564,662 S | 3/2008 | Moses et al. | | 2004/0260281 A1 | 12/2004 | Baxter, III et al. |
| 7,338,526 B2 | 3/2008 | Steinberg | | 2005/0004564 A1 | 1/2005 | Wham et al. |
| 7,342,754 B2 | 3/2008 | Fitzgerald et al. | | 2005/0004569 A1 | 1/2005 | Witt et al. |
| 7,344,268 B2 | 3/2008 | Jigamian | | 2005/0033278 A1 | 2/2005 | McClurken et al. |
| D567,943 S | 4/2008 | Moses et al. | | 2005/0059934 A1 | 3/2005 | Wenchell et al. |
| 7,367,976 B2 | 5/2008 | Lawes et al. | | 2005/0096645 A1 | 5/2005 | Wellman et al. |
| 7,377,920 B2 | 5/2008 | Buysse et al. | | 2005/0101951 A1 | 5/2005 | Wham et al. |
| 7,384,420 B2 | 6/2008 | Dycus et al. | | 2005/0101952 A1 | 5/2005 | Lands et al. |
| 7,384,421 B2 | 6/2008 | Hushka | | 2005/0113818 A1 | 5/2005 | Sartor et al. |
| 7,396,336 B2 | 7/2008 | Orszulak et al. | | 2005/0113819 A1 | 5/2005 | Wham et al. |
| D575,395 S | 8/2008 | Hushka | | 2005/0113826 A1 | 5/2005 | Johnson et al. |
| D575,401 S | 8/2008 | Hixson et al. | | 2005/0149017 A1 | 7/2005 | Dycus |
| 7,435,249 B2 | 10/2008 | Buysse et al. | | 2005/0149151 A1 | 7/2005 | Orszulak et al. |
| 7,442,193 B2 | 10/2008 | Shields et al. | | 2005/0154387 A1 | 7/2005 | Moses et al. |
| 7,442,194 B2 | 10/2008 | Dumbauld et al. | | 2005/0187547 A1 | 8/2005 | Sugi |
| 7,445,621 B2 | 11/2008 | Dumbauld et al. | | 2005/0197659 A1 | 9/2005 | Bahney |
| 7,458,972 B2 | 12/2008 | Keppel | | 2005/0203504 A1 | 9/2005 | Wham et al. |
| 7,473,253 B2 | 1/2009 | Dycus et al. | | 2006/0052778 A1 | 3/2006 | Chapman et al. |
| 7,481,810 B2 | 1/2009 | Dumbauld et al. | | 2006/0052779 A1 | 3/2006 | Hammill |
| 7,487,780 B2 | 2/2009 | Hooven | | 2006/0064085 A1 | 3/2006 | Schechter et al. |
| 7,491,201 B2 | 2/2009 | Shields et al. | | 2006/0064086 A1 | 3/2006 | Odom |
| 7,491,202 B2 | 2/2009 | Odom et al. | | 2006/0074417 A1 | 4/2006 | Cunningham et al. |
| 7,500,975 B2 | 3/2009 | Cunningham et al. | | 2006/0079888 A1 | 4/2006 | Mulier et al. |
| 7,510,556 B2 | 3/2009 | Nguyen et al. | | 2006/0079890 A1 | 4/2006 | Guerra |
| 7,513,898 B2 | 4/2009 | Johnson et al. | | 2006/0079891 A1 | 4/2006 | Arts et al. |
| 7,540,872 B2 | 6/2009 | Schechter et al. | | 2006/0079933 A1 | 4/2006 | Hushka et al. |
| 7,549,995 B2 | 6/2009 | Schultz | | 2006/0084973 A1 | 4/2006 | Hushka |
| 7,553,312 B2 | 6/2009 | Tetzlaff et al. | | 2006/0089670 A1 | 4/2006 | Hushka |
| 2002/0013583 A1 | 1/2002 | Camran et al. | | 2006/0116675 A1 | 6/2006 | McClurken et al. |
| 2002/0049442 A1 | 4/2002 | Roberts et al. | | 2006/0129146 A1 | 6/2006 | Dycus et al. |
| 2002/0099372 A1 | 7/2002 | Schulze et al. | | 2006/0167450 A1 | 7/2006 | Johnson et al. |
| 2002/0107517 A1 | 8/2002 | Witt et al. | | 2006/0167452 A1 | 7/2006 | Moses et al. |
| 2002/0111624 A1 | 8/2002 | Witt et al. | | 2006/0173452 A1 | 8/2006 | Buysse et al. |
| 2002/0188294 A1 | 12/2002 | Couture et al. | | 2006/0189981 A1 | 8/2006 | Dycus et al. |
| 2003/0014052 A1 | 1/2003 | Buysse et al. | | 2006/0190035 A1 | 8/2006 | Hushka et al. |
| 2003/0014053 A1 | 1/2003 | Nguyen et al. | | 2006/0217709 A1 | 9/2006 | Couture et al. |
| 2003/0018331 A1 | 1/2003 | Dycus et al. | | 2006/0229666 A1 | 10/2006 | Suzuki et al. |
| 2003/0018332 A1 | 1/2003 | Schmaltz et al. | | 2006/0253126 A1 | 11/2006 | Bjerken et al. |
| 2003/0032956 A1 | 2/2003 | Lands et al. | | 2006/0259036 A1 | 11/2006 | Tetzlaff et al. |
| 2003/0065358 A1 * | 4/2003 | Frecker et al. ............... 606/205 | | 2006/0264922 A1 | 11/2006 | Sartor et al. |
| 2003/0069570 A1 | 4/2003 | Witzel et al. | | 2006/0264931 A1 | 11/2006 | Chapman et al. |
| 2003/0069571 A1 | 4/2003 | Treat et al. | | 2006/0283093 A1 | 12/2006 | Petrovic et al. |
| 2003/0078578 A1 | 4/2003 | Truckai et al. | | 2006/0287641 A1 | 12/2006 | Perlin |
| 2003/0109875 A1 | 6/2003 | Tetzlaff et al. | | 2007/0016182 A1 | 1/2007 | Lipson et al. |
| 2003/0114851 A1 | 6/2003 | Truckai et al. | | 2007/0016187 A1 | 1/2007 | Weinberg et al. |
| 2003/0139741 A1 | 7/2003 | Goble et al. | | 2007/0043352 A1 | 2/2007 | Garrison et al. |
| 2003/0139742 A1 | 7/2003 | Wampler et al. | | 2007/0043353 A1 | 2/2007 | Dycus et al. |
| 2003/0158548 A1 | 8/2003 | Phan et al. | | 2007/0060919 A1 | 3/2007 | Isaacson et al. |

| | | | | | | |
|---|---|---|---|---|---|---|
| 2007/0062017 A1 | 3/2007 | Dycus et al. | DE | 4303882 | 8/1994 | |
| 2007/0074807 A1 | 4/2007 | Guerra | DE | 4403252 | 8/1995 | |
| 2007/0078456 A1 | 4/2007 | Dumbauld et al. | DE | 19515914 | 7/1996 | |
| 2007/0078458 A1 | 4/2007 | Dumbauld et al. | DE | 29616210 | 1/1997 | |
| 2007/0078459 A1 | 4/2007 | Johnson et al. | DE | 19608716 | 4/1997 | |
| 2007/0088356 A1 | 4/2007 | Moses et al. | DE | 19751106 | 5/1998 | |
| 2007/0106295 A1 | 5/2007 | Garrison et al. | DE | 19751108 | 5/1999 | |
| 2007/0106297 A1 | 5/2007 | Dumbauld et al. | DE | 19738457 | 1/2009 | |
| 2007/0118111 A1 | 5/2007 | Weinberg | EP | 0364216 | 4/1990 | |
| 2007/0118115 A1 | 5/2007 | Artale et al. | EP | 0467501 | 1/1992 | |
| 2007/0142833 A1 | 6/2007 | Dycus et al. | EP | 0518230 | 12/1992 | |
| 2007/0142834 A1 | 6/2007 | Dumbauld | EP | 0541930 | 5/1993 | |
| 2007/0156139 A1 | 7/2007 | Schechter et al. | EP | 0572131 | 12/1993 | |
| 2007/0156140 A1 | 7/2007 | Baily | EP | 0584787 | 3/1994 | |
| 2007/0173811 A1 | 7/2007 | Couture et al. | EP | 0589453 | 3/1994 | |
| 2007/0173814 A1 | 7/2007 | Hixson et al. | EP | 0589555 | 3/1994 | |
| 2007/0179499 A1 | 8/2007 | Garrison | EP | 0623316 | 11/1994 | |
| 2007/0198011 A1 | 8/2007 | Sugita | EP | 0624348 | 11/1994 | |
| 2007/0213712 A1 | 9/2007 | Buysse et al. | EP | 0650701 | 5/1995 | |
| 2007/0255279 A1 | 11/2007 | Buysse et al. | EP | 0694290 | 3/1996 | |
| 2007/0260235 A1 | 11/2007 | Podhajsky | EP | 0717966 | 6/1996 | |
| 2007/0260238 A1 | 11/2007 | Guerra | EP | 0754437 | 3/1997 | |
| 2007/0260241 A1 | 11/2007 | Dalla Betta et al. | EP | 0517243 | 9/1997 | |
| 2007/0260242 A1 | 11/2007 | Dycus et al. | EP | 0853922 | 7/1998 | |
| 2007/0265616 A1 | 11/2007 | Couture et al. | EP | 0875209 | 11/1998 | |
| 2008/0004616 A1 | 1/2008 | Patrick | EP | 0878169 | 11/1998 | |
| 2008/0009860 A1 | 1/2008 | Odom | EP | 0887046 | 1/1999 | |
| 2008/0015575 A1 | 1/2008 | Odom et al. | EP | 0923907 | 6/1999 | |
| 2008/0021450 A1 | 1/2008 | Couture | EP | 0986990 | 3/2000 | |
| 2008/0033428 A1 | 2/2008 | Artale et al. | EP | 1034747 | 9/2000 | |
| 2008/0039835 A1 | 2/2008 | Johnson et al. | EP | 1034748 | 9/2000 | |
| 2008/0039836 A1 | 2/2008 | Odom et al. | EP | 1025807 | 10/2000 | |
| 2008/0045947 A1 | 2/2008 | Johnson et al. | EP | 1034746 | 10/2000 | |
| 2008/0058802 A1 | 3/2008 | Couture et al. | EP | 1050278 | 11/2000 | |
| 2008/0082100 A1 | 4/2008 | Orton et al. | EP | 1053719 | 11/2000 | |
| 2008/0091189 A1 | 4/2008 | Carlton | EP | 1053720 | 11/2000 | |
| 2008/0114356 A1 | 5/2008 | Johnson et al. | EP | 1055399 | 11/2000 | |
| 2008/0167651 A1 | 7/2008 | Tetzlaff et al. | EP | 1055400 | 11/2000 | |
| 2008/0195093 A1 | 8/2008 | Couture et al. | EP | 1080694 | 3/2001 | |
| 2008/0215051 A1 | 9/2008 | Buysse et al. | EP | 1082944 | 3/2001 | |
| 2008/0243120 A1 | 10/2008 | Lawes et al. | EP | 1159926 | 12/2001 | |
| 2008/0249527 A1 | 10/2008 | Couture | EP | 1177771 | 2/2002 | |
| 2008/0312653 A1 | 12/2008 | Arts et al. | EP | 1301135 | 4/2003 | |
| 2008/0319442 A1 | 12/2008 | Unger et al. | EP | 1330991 | 7/2003 | |
| 2009/0012520 A1 | 1/2009 | Hixson et al. | EP | 1486177 | 6/2004 | |
| 2009/0018535 A1 | 1/2009 | Schechter et al. | EP | 1472984 | 11/2004 | |
| 2009/0024126 A1 | 1/2009 | Artale et al. | EP | 0774232 | 1/2005 | |
| 2009/0043304 A1 | 2/2009 | Tetzlaff et al. | EP | 1527747 | 5/2005 | |
| 2009/0048596 A1 | 2/2009 | Shields et al. | EP | 1530952 | 5/2005 | |
| 2009/0062794 A1 | 3/2009 | Buysse et al. | EP | 1532932 | 5/2005 | |
| 2009/0082766 A1 | 3/2009 | Unger et al. | EP | 1535581 | 6/2005 | |
| 2009/0082767 A1 | 3/2009 | Unger et al. | EP | 1609430 | 12/2005 | |
| 2009/0082769 A1 | 3/2009 | Unger et al. | EP | 1632192 | 3/2006 | |
| 2009/0088738 A1 | 4/2009 | Guerra et al. | EP | 1642543 | 4/2006 | |
| 2009/0088739 A1 | 4/2009 | Hushka et al. | EP | 1645238 | 4/2006 | |
| 2009/0088740 A1 | 4/2009 | Guerra et al. | EP | 1645240 | 4/2006 | |
| 2009/0088741 A1 | 4/2009 | Hushka et al. | EP | 1649821 | 4/2006 | |
| 2009/0088744 A1 | 4/2009 | Townsend | EP | 1707143 | 10/2006 | |
| 2009/0088745 A1 | 4/2009 | Hushka et al. | EP | 1769765 | 4/2007 | |
| 2009/0088746 A1 | 4/2009 | Hushka et al. | EP | 1769766 | 4/2007 | |
| 2009/0088747 A1 | 4/2009 | Hushka et al. | EP | 1929970 | 6/2008 | |
| 2009/0088748 A1 | 4/2009 | Guerra et al. | EP | 1683496 | 12/2008 | |
| 2009/0088749 A1 | 4/2009 | Hushka et al. | GB | 623316 | 5/1949 | |
| 2009/0088750 A1 | 4/2009 | Hushka et al. | GB | 1490585 | 11/1977 | |
| 2009/0112206 A1 | 4/2009 | Dumbauld et al. | GB | 2214430 A | 6/1989 | |
| 2009/0131934 A1 | 5/2009 | Odom et al. | GB | 2213416 A | 8/1989 | |
| 2009/0149853 A1 | 6/2009 | Shields et al. | JP | 61-501068 | 9/1984 | |
| 2009/0149854 A1 | 6/2009 | Cunningham et al. | JP | 65-502328 | 3/1992 | |
| 2009/0171350 A1 | 7/2009 | Dycus et al. | JP | 5-5106 | 1/1993 | |
| 2009/0171353 A1 | 7/2009 | Johnson et al. | JP | 5-40112 | 2/1993 | |
| 2009/0182327 A1 | 7/2009 | Unger | JP | 06343644 A2 | 12/1994 | |
| 2009/0187188 A1 | 7/2009 | Guerra et al. | JP | 07265328 A2 | 10/1995 | |
| | | | JP | 08056955 A2 | 3/1996 | |
| | FOREIGN PATENT DOCUMENTS | | JP | 08252263 A2 | 10/1996 | |
| DE | 2415263 | 10/1975 | JP | 09010223 A2 | 1/1997 | |
| DE | 2514501 | 10/1976 | JP | 11244298 A2 | 9/1999 | |
| DE | 2627679 | 1/1977 | JP | 2000-342599 A2 | 12/2000 | |
| DE | 3612646 | 4/1987 | JP | 2000-350732 A2 | 12/2000 | |
| DE | 8712328 | 3/1988 | JP | 2001-008944 A2 | 1/2001 | |

| | | |
|---|---|---|
| JP | 2001-029356 A2 | 2/2001 |
| JP | 2001-128990 A2 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 | 3/2001 |
| WO | WO 01/54604 | 8/2001 |
| WO | WO 02/07627 | 1/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98957771 dated Aug. 9, 2001.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Sep. 28, 2005 .
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05019429.9 dated May 6, 2008.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
Int'l Search Report—extended-EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008515.6 dated Jan. 8, 2009.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended-EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 014016 dated Jan. 28, 2008.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report PCT/US98/18640 dated Dec. 17, 1998.
Int'l Search Report PCT/US98/23950 dated Dec. 29, 1998.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US03/28534 dated Dec. 19, 2003.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report EP 09 152267.2 Dated Jun. 15, 2009.
Int'l Search Report EP 09 152898.4 Dated Jun. 10, 2009.
Int'l Search Report PCT/US09/032690 dated Jun. 16, 2009.

* cited by examiner

APPARATUS, SYSTEM, AND METHOD FOR PERFORMING AN ELECTROSURGICAL PROCEDURE

BACKGROUND

1. Technical Field

The present disclosure relates to an apparatus, system, and method for performing an electrosurgical procedure. More particularly, the present disclosure relates to an apparatus, system, and method for performing an electrosurgical procedure that employs an electrosurgical apparatus that includes an end effector assembly configured for use with various size access ports.

2. Description of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue As an alternative to open electrosurgical forceps for use with open surgical procedures, many modern surgeons use endoscopes and endoscopic electrosurgical apparatus (e.g., endoscopic forceps) or laparoscopic forceps for remotely accessing organs through smaller, puncture-like incisions. As a direct result thereof, patients tend to benefit from less scarring and reduced healing time. Typically, the forceps are inserted into the patient through one or more various types of cannulas or access ports (typically having an opening that ranges from about five millimeters to about twelve millimeters) that has been made with a trocar; as can be appreciated, smaller cannulas are usually preferred.

Forceps that are configured for use with small cannulas (e.g., cannulas less than five millimeters) may present design challenges for a manufacturer of electrosurgical instruments.

SUMMARY

According to an embodiment of the present disclosure, a bipolar forceps includes a housing having a shaft extending therefrom including an end effector assembly at a distal end thereof. The end effector assembly has a wheel assembly opposing a jaw member and having a pair of opposing wheels configured to facilitate movement of the wheel assembly relative to the jaw member. A drive rod is operably coupled at a proximal end to a movable handle and at a distal end to the wheel assembly. The movable handle is movable relative to a stationary handle to move the wheel assembly relative to the jaw member. At least one electrically conductive tissue sealing plate is disposed on each of the wheel assembly and the jaw member and is adapted to connect to an electrosurgical energy source configured to deliver electrosurgical energy to tissue held between the wheel assembly and the jaw member to effect a tissue seal.

According to another embodiment of the present disclosure, a bipolar forceps includes a housing having a shaft that extends therefrom including an end effector assembly at a distal end thereof. The end effector assembly has a wheel assembly opposing a jaw member. The wheel assembly has a pair of opposing wheels configured to facilitate movement of the wheel assembly relative to the jaw member. A drive rod is operably coupled at a proximal end to a movable handle disposed within a housing and at a distal end to a mechanical interface disposed between the pair of wheels. The movable handle is movable relative to a stationary handle disposed within the housing to cause proximal and distal movement of the drive rod. The pair of wheels is configured to rotate about the mechanical interface such that proximal movement of the drive rod causes rotation of the pair of wheels in a first direction to move the wheel assembly proximally relative to the jaw member, and distal movement of the drive rod causes rotation of the pair of wheels in a second direction to move the wheel assembly distally relative to the jaw member. At least one electrically conductive tissue sealing plate is disposed on each of the wheel assembly and the jaw member. The at least one electrically conductive tissue sealing plate is adapted to connect to an electrosurgical energy source configured to deliver electrosurgical energy to tissue held between the wheel assembly and the jaw member via the at least one electrically conductive tissue sealing plate to effect a tissue seal.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As noted above, it may prove useful in the arts to provide an electrosurgical apparatus that is suitable for use with various access ports, including but not limited to those that are greater than and/or less than five millimeters. With this purpose in mind, the present disclosure includes an electrosurgical forceps that includes a drive rod operably coupled to a wheel assembly. The wheel assembly is associated with a jaw member such that the wheel assembly and jaw member are configured to move relative to each other to selectively form a closed loop electrical circuit such that a desired tissue effect (e.g., tissue seal) may be achieved.

Figure 1:
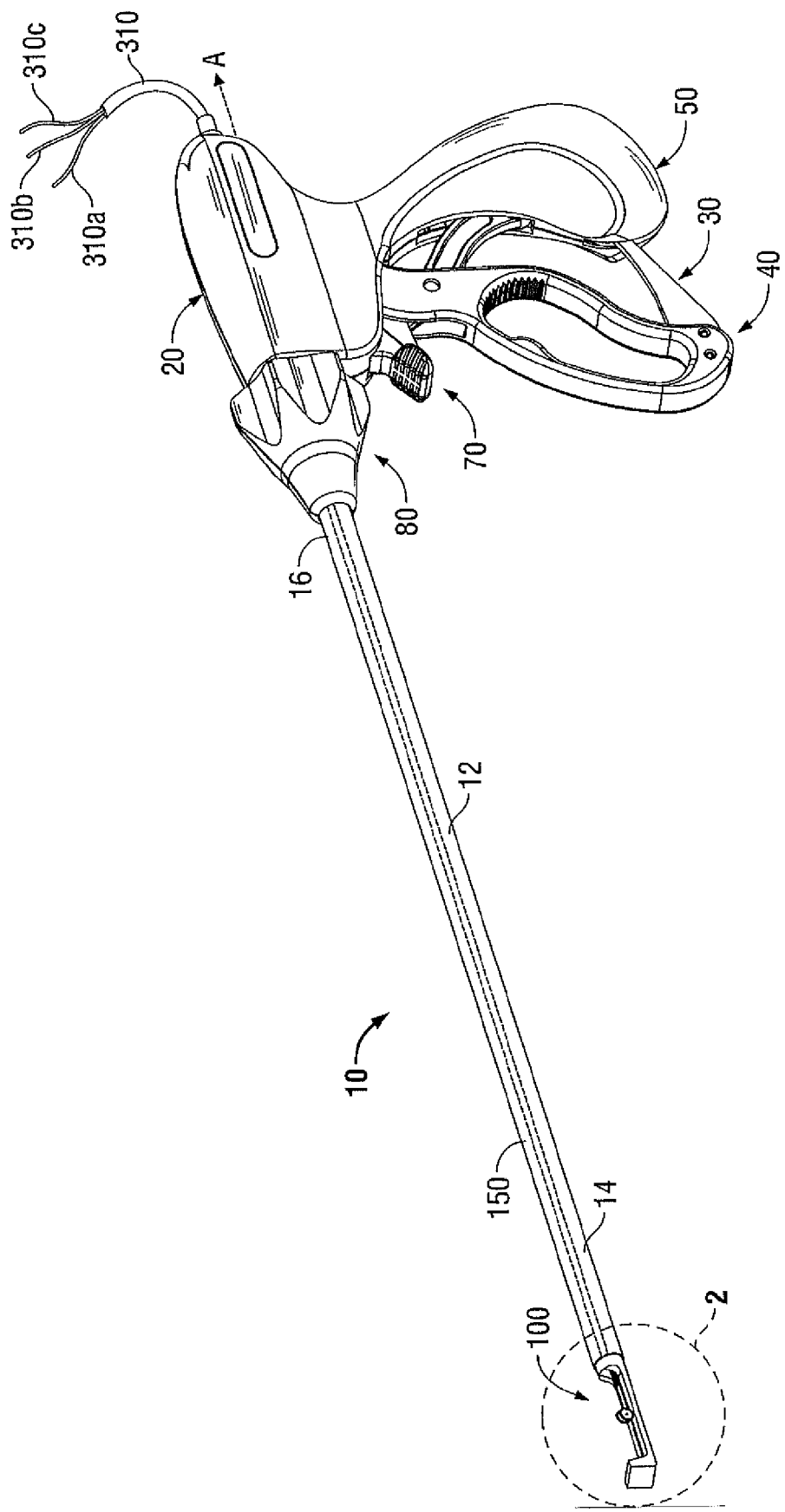
FIG. 1 is a right perspective view of an endoscopic bipolar forceps showing a housing, a shaft, and an end effector assembly in accordance with the present disclosure.
Figure 2:
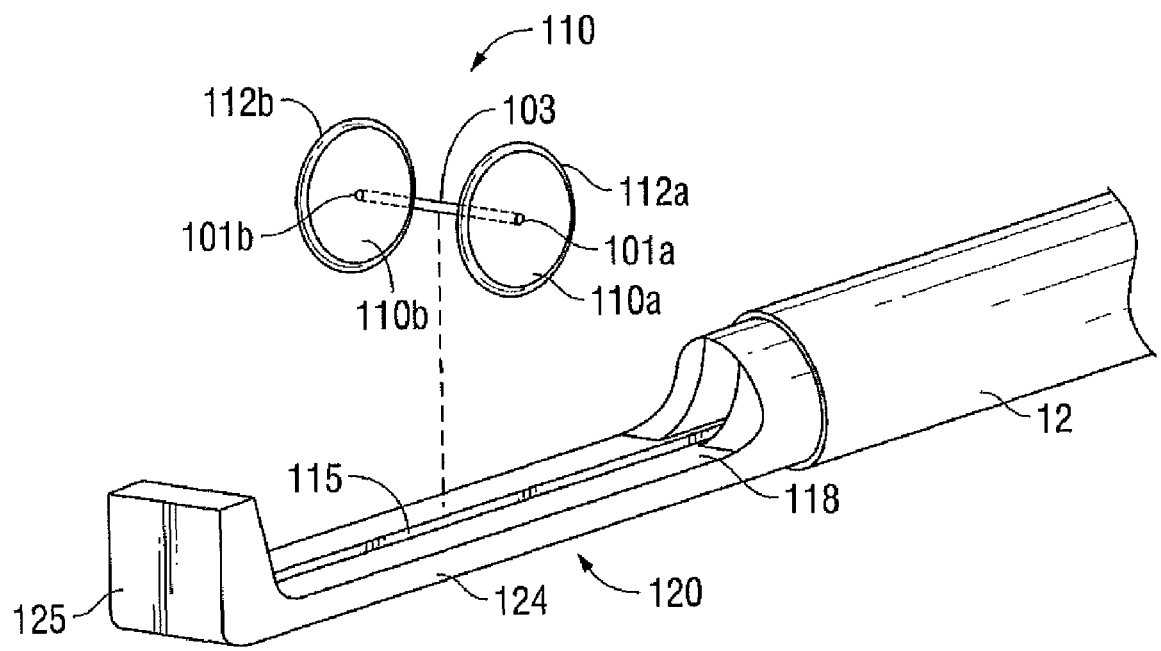
FIG. 2 is an enlarged, right perspective view of the end effector assembly of FIG. 1.

Turning now to FIGS. 1 and 2, an embodiment of an laparoscopic bipolar forceps 10 is shown for use with various surgical procedures and generally includes a housing 20, a handle assembly 30, a rotating assembly 80, a trigger assembly 70, a shaft 12, a drive rod 150 (shown in phantom), and an end effector assembly 100. The end effector assembly 100 includes a wheel assembly 110 having opposing wheels 110a and 110b configured to engage a jaw member 120 such that wheels 110a, 110b rotate to facilitate movement of wheel assembly 110 and jaw member 120 relative to each other to mutually cooperate to grasp, seal, and divide large tubular vessels and large vascular tissues. As best shown in FIG. 2, wheels 110a and 110b include electrically conductive seal plates 112a and 112b circumferentially disposed thereon, respectively, for purposes of sealing tissue. Each of wheels 110a and 110b also includes an aperture 101a and 101b, respectively, defined therethrough that secures a rotation pin 103 therebetween. As will be discussed in further detail below, wheels 110a and 110b rotate about rotation pin 103 to facilitate movement of wheel assembly 110 relative to jaw member 120. Although the majority of the figure drawings depict a bipolar forceps 10 for use in connection with laparoscopic surgical procedures, the present disclosure may be used for more traditional open surgical procedures or endoscopic procedures. For the purposes herein, the forceps 10 is described in terms of an laparoscopic instrument; however, it is contemplated that an open version or endoscopic version of the forceps may also include the same or similar operating components and features as described below.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 is operatively connected to the housing 20 and is rotatable approximately 180 degrees in either direction about a longitudinal axis "A" (See FIG. 1).

Shaft 12 has a distal end 14 configured to mechanically engage the end effector assembly 100 and a proximal end 16 which mechanically engages the housing 20. In the drawings and in the descriptions that follow, the term "proximal", as is traditional, will refer to the end of the forceps 10 that is closer to the user, while the term "distal" will refer to the end that is further from the user.

Figure 4A:
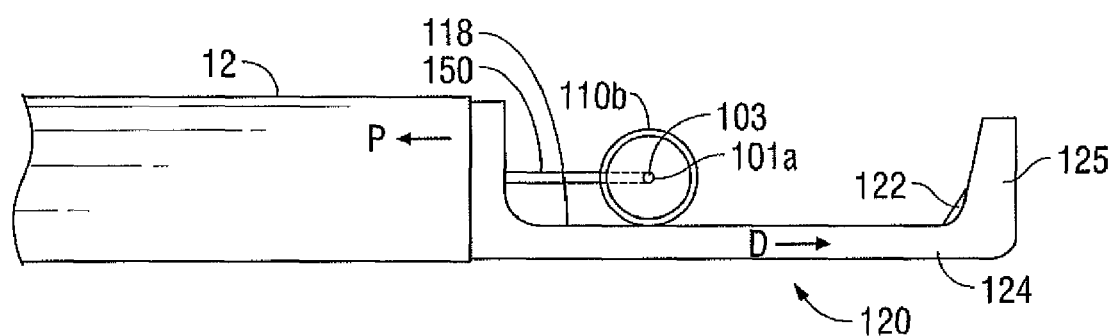
FIGS. 4A and 4B are enlarged, side views of the end effector assembly of FIG. 1.
Figure 4B:
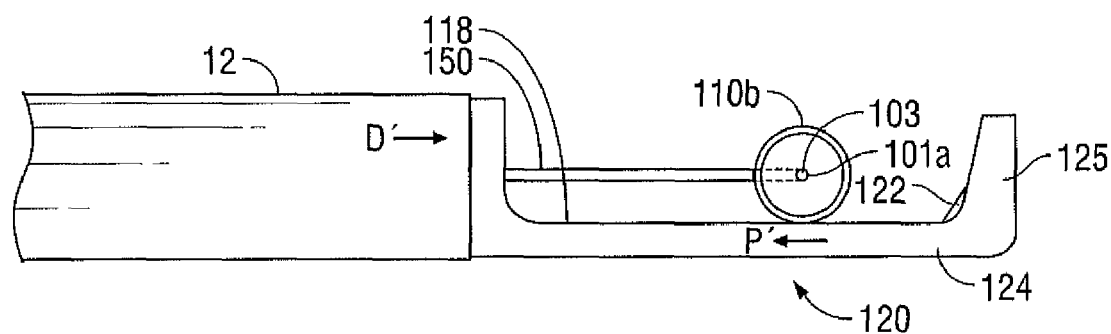

Drive rod 150 is slidably disposed in shaft 12. A proximal end of drive rod 150 is operatively coupled to handle assembly 30 and a distal end of drive rod 150 is operatively coupled to end effector assembly 100. More specifically, wheel assembly 110 is anchored to a distal end of drive rod 150 via the rotation pin 103, as best shown in FIGS. 4A and 4B. Actuation of movable handle 40 relative to stationary handle 50 imparts proximal and distal movement of drive rod 150, which, in turn, urges wheel assembly 110 proximally and distally, respectively, relative to jaw member 120, to grasp tissue therebetween. End effector assembly 100 is configured to grasp tissue between wheel assembly 110 and jaw member 120 when wheel assembly 110 is in a substantially distal position relative to jaw member 120 (see FIG. 4B), in a substantially proximal position relative to jaw member 120 (see FIG. 4A), and/or in any position disposed therebetween relative to jaw member 120.

More specifically, and with reference to FIGS. 4A and 4B, wheel assembly 110 is operable by the drive rod 150 such that drive rod 150 urges wheel assembly 110 in the proximal and distal directions, as indicated by directional arrows P and D', respectively. More specifically, distal movement of drive rod 150 causes wheels 110a, 110b to rotate clock-wise to facilitate distal movement of wheel assembly 110 relative to jaw member 120. Conversely, proximal movement of drive rod 150 causes wheels 110a, 110b to rotate counter-clock-wise to facilitate proximal movement of wheel assembly 110 relative to jaw member 120.

In some embodiments, actuation of handle assembly 30 is configured to translate proximal and distal movement of jaw member 120 to facilitate functionality substantially as described above with respect to proximal and distal movement of wheel assembly 100. More specifically, proximal and distal movement of jaw member 120 relative to wheel assembly 110 may be imparted via actuation of moveable handle 40 relative to stationary handle 50. With this purpose in mind, forceps 10 may include any number of electrical connections, configurations, and/or components (e.g., resistors, capacitors, inductors, rheostats, etc.), mechanical connections, configurations, and/or components (e.g., gears, links, springs, rods, etc.), and/or electro-mechanical connections, configurations, and/or components such that forceps 10 may function as intended.

More specifically, and with continued reference to FIGS. 4A and 4B, proximal and distal movement of jaw member 120 relative to wheel assembly 110 may be imparted via actuation of moveable handle 40 relative to stationary handle 50, as indicated by directional arrows P' and D, respectively. More specifically, distal movement of jaw member 120 causes wheels 110a, 110b to rotate counter clock-wise to facilitate proximal movement of wheel assembly 110 relative to jaw member 120. Conversely, proximal movement of jaw member 120 causes wheels 110a, 110b to rotate clock-wise to facilitate distal movement of wheel assembly 110 relative to jaw member 120.

Forceps 10 includes an electrosurgical cable 310 that connects the forceps 10 to a source of electrosurgical energy, e.g., a generator (not shown). One such source of electrosurgical energy is described in commonly-owned U.S. Pat. No. 6,033, 399 entitled "ELECTROSURGICAL GENERATOR WITH ADAPTIVE POWER CONTROL". Cable 310 is internally divided into cable leads 310a, 310b, and 310c, which are designed to transmit electrical potentials through their respective feed paths through the forceps 10 to the end effector assembly 100. More specifically, the source of electrosurgical energy transmits electrosurgical energy, which may be in the form of a wave or signal/pulse, via one or more cables (e.g., cable 310) to the end effector assembly 100.

For a more detailed description of handle assembly 30, movable handle 40, rotating assembly 80, and electrosurgical cable 310 (including line-feed configurations and/or connections) reference is made to commonly owned Patent Publication No., 2003-0229344, filed on Feb. 20, 2003, entitled VESSEL SEALER AND DIVIDER AND METHOD OF MANUFACTURING THE SAME.

Figure 5:
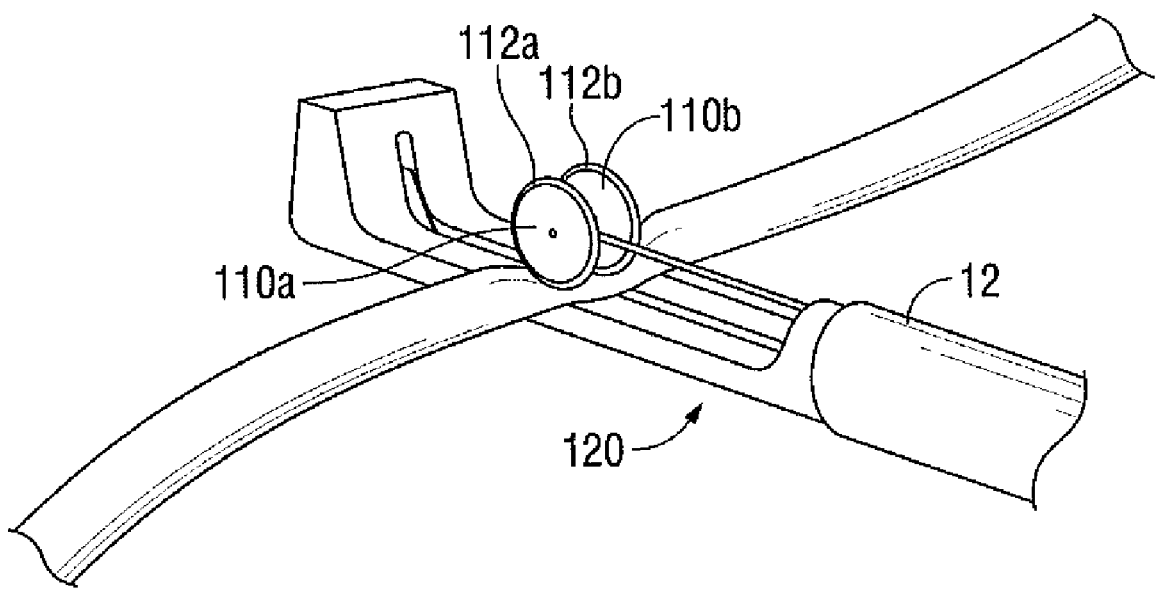
FIG. 5 is an enlarged, rear perspective view of the end effector shown grasping tissue.

As noted above, movable handle 40 of handle assembly 30 is operatively coupled to drive rod 150 which, together, mechanically cooperate to impart proximal and distal movement of the wheel assembly 110 relative to jaw member 120 such that wheel assembly 110 and jaw member 120 cooperate to grasp tissue therebetween (see FIG. 5). With this purpose in mind, drive rod 150 may be configured to incorporate any number of electrical connections, configurations, and/or components (e.g., resistors, capacitors, inductors, rheostats, etc.), mechanical connections, configurations, and/or components (e.g., gears, links, springs, rods, etc.), and/or electro-mechanical connections, configurations, and/or components such that forceps 10 may function as intended.

Jaw member 120 includes an insulative jaw housing 124 and an electrically conductive seal plate 118. Insulator 124 is configured to securely engage the electrically conductive seal plate 118. Seal plates 112a, 112b of wheels 110a, 110b and seal plate 118 may be manufactured from stamped steel. The may be accomplished by stamping, by overmolding, by overmolding a stamped electrically conductive seal plate and/or by overmolding a metal injection molded seal plate. All of these manufacturing techniques produce an electrode having a seal plate 118 that is substantially surrounded by the insulating substrate.

The insulator 124, seal plates 112a, 112b, 118, and the wheels 110a, 110b may be configured to limit and/or reduce many of the known undesirable effects related to tissue sealing, e.g., flashover, thermal spread and stray current dissipation. In other embodiments, wheels 110a, 110b and jaw member 120 may be manufactured from a ceramic-like material and the electrically conductive surface 112a, 112b, and 118 are coated onto the ceramic-like wheels 110a, 110b and jaw member 120, respectively.

To prevent short-circuiting from occurring between the seal plates 112a, 112b, and 118 and either or both of the rotation pin 103 and the drive rod 150, the rotation pin 103 and/or drive rod 150 may be provided with an insulative material (not explicitly shown) applied thereto and/or may be formed of a non-conductive material.

FIG. 5 shows the forceps 10 grasping tissue. In one embodiment, and as noted hereinabove, actuation of moveable handle 40 causes distal and proximal movement of drive rod 150, which, in turn, causes corresponding distal and proximal movement of wheel assembly 110 relative to jaw member 120 to grasp and seal tissue disposed therebetween, as shown in FIG. 5. In another embodiment and as noted hereinabove, actuation of moveable handle causes distal and proximal movement of jaw member 120 relative to wheel assembly 110, via any suitable configuration discussed hereinabove with respect to jaw member 120, to grasp and seal tissue therebetween.

The wheel assembly 110 configuration of end effector assembly 100 allows the wheels 110a, 110b to be rotated to manipulate tissue until sealing is desired. This enables the user to position and re-position the forceps 10 prior to activation and sealing. Once tissue is fully compressed between wheels 110a, 110b and jaw member 120, or more specifically between sealing surfaces 112a, 112b, and 118, the forceps 10 are now ready for selective application of electrosurgical energy and subsequent separation of the tissue. More specifically, the source of electrosurgical energy, discussed hereinabove, transmits electrosurgical energy, which may be in the form of a wave or signal/pulse, via one or more cables (e.g., cable 310) to one or both of seal plates 112a, 112b and 118. For example, a first electrical potential (e.g., "+") may be transmitted to sealing surfaces 112a, 112b and a second electrical potential (e.g., "−") may be transmitted to sealing surface 118. Electrosurgical energy may be transmitted to each of the seal plates simultaneously or consecutively.

Figure 3:
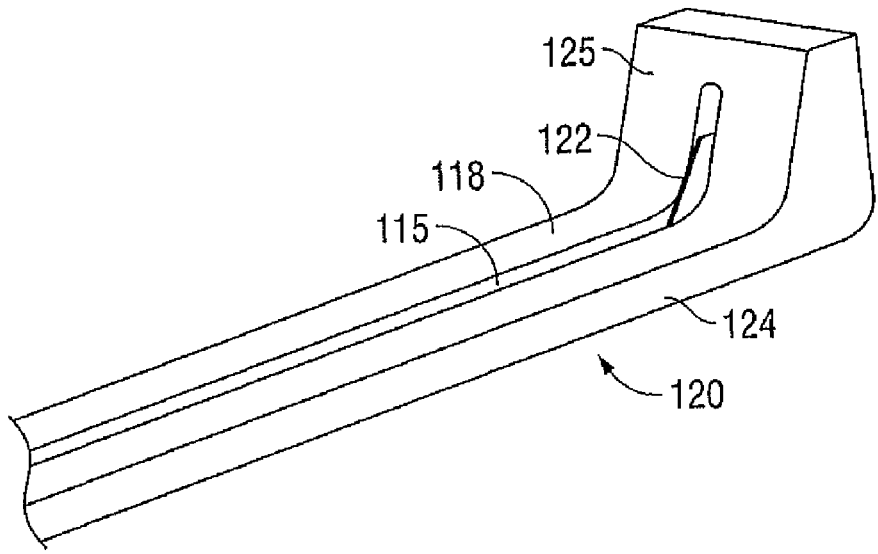
FIG. 3 is an enlarged, left perspective view of the end effector assembly of FIG. 1.

As best shown in FIG. 3, a knife channel 115 runs through the center of jaw member 120 such that a blade 122 may cut tissue grasped between wheel assembly 110 and jaw member 120. More specifically, the blade 122 advances through knife channel 115 when activated (e.g., via the trigger assembly 70) to progressively and selectively divide tissue along an ideal tissue plane in a precise manner to effectively and reliably divide the tissue. In embodiments, forceps 10 may be configured such that blade 122 may only be advanced through knife channel 115 to cut tissue when wheel assembly 110 is positioned at certain locations along jaw member 120 (e.g., in a grasping position, a distal most position, a proximal most position, etc.) thus preventing accidental or premature activation of the blade 122 through tissue.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A bipolar forceps, comprising:
 a housing having a shaft that extends therefrom including an end effector assembly at a distal end thereof, the end effector assembly having a wheel assembly opposing a jaw member, the wheel assembly having a pair of opposing wheels configured to facilitate movement of the wheel assembly relative to the jaw member;
 a drive rod operably coupled at a proximal end to a movable handle and at a distal end to the wheel assembly, the movable handle movable relative to a stationary handle to move the wheel assembly relative to the jaw member; and
 at least one electrically conductive tissue sealing plate disposed on each of the wheel assembly and the jaw member, the electrically conductive tissue sealing plates adapted to connect to an electrosurgical energy source configured to deliver electrosurgical energy to tissue held between the wheel assembly and the jaw member to effect a tissue seal;
 wherein the drive rod is operably coupled at a distal end to a mechanical interface disposed between the pair of wheels, the pair of wheels configured to rotate about the mechanical interface such that proximal movement of the drive rod causes rotation of the pair of wheels in a first direction to move the wheel assembly proximally relative to the jaw member, and distal movement of the drive rod causes rotation of the pair of wheels in a second direction to move the wheel assembly distally relative to the jaw member.

2. A bipolar forceps according to claim 1, wherein the electrosurgical energy source is adapted to deliver a first electrical potential to the at least one electrically conductive tissue sealing plate disposed on the wheel assembly and a second electrical potential to the at least one electrically conductive tissue sealing plate disposed on the jaw member.

3. A bipolar forceps according to claim 1, wherein the end effector assembly is configured to at least one of grasp tissue between the wheel assembly and the jaw member and selectively conduct energy through tissue held between the wheel assembly and the jaw member when the wheel assembly is in a predetermined position relative to the jaw member.

4. A bipolar forceps according to claim 1, wherein the jaw member is movable proximally and distally relative to the wheel assembly upon actuation of the movable handle.

5. A bipolar forceps according to claim 1, further comprising a trigger disposed within the housing and in electromechanical cooperation with the source of electrosurgical energy, the trigger allowing a user to selectively supply bipolar energy to each of the wheel assembly and the jaw member to effect the tissue seal.

6. A bipolar forceps according to claim 1, further comprising a rotating assembly for rotating the end effector assembly about the longitudinal axis defined through the shaft.

7. A bipolar forceps according to claim 1, further comprising a knife assembly configured to cut tissue along the tissue seal when the wheel assembly is in a predetermined position relative to the jaw member.

8. A bipolar forceps according to claim 1, wherein the movable handle is movable between a closed position to cause the drive rod to move the wheel assembly distally relative to the jaw member and an open position to cause the drive rod to move the wheel assembly proximally relative to the jaw member.

9. A bipolar forceps, comprising:
- a housing having a shaft that extends therefrom including an end effector assembly at a distal end thereof the end effector assembly having a wheel assembly opposing a jaw member, the wheel assembly having a pair of opposing wheels configured to facilitate movement of the wheel assembly relative to the jaw member;
- a drive rod operably coupled at a proximal end to a movable handle disposed within a housing and at a distal end to a mechanical interface disposed between the pair of wheels, the movable handle movable relative to a stationary handle disposed within the housing to cause proximal and distal movement of the drive rod, the pair of wheels configured to rotate about the mechanical interface such that proximal movement of the drive rod causes rotation of the pair of wheels in a first direction to move the wheel assembly proximally relative to the jaw member, and distal movement of the drive rod causes rotation of the pair of wheels in a second direction to move the wheel assembly distally relative to the jaw member; and
- at least one electrically conductive tissue sealing plate disposed on each of the wheel assembly and the jaw member, the electrically conductive tissue sealing plates adapted to connect to an electrosurgical energy source configured to deliver electrosurgical energy to tissue held between the wheel assembly and the jaw member to effect a tissue seal.

10. A bipolar forceps according to claim 9, wherein the jaw member is movable proximally and distally relative to the wheel assembly upon actuation of the movable handle.

11. A bipolar forceps according to claim 9, wherein the electrosurgical energy source is adapted to deliver a first electrical potential to the at least one electrically conductive tissue sealing plate disposed on the wheel assembly and a second electrical potential to the at least one electrically conductive tissue sealing plate disposed on the jaw member.

12. A bipolar forceps according to claim 9, wherein the end effector assembly is configured to at least one of grasp tissue between the wheel assembly and the jaw member and selectively conduct energy through tissue held between the wheel assembly and the jaw member when the wheel assembly is in a predetermined position relative to the jaw member.

13. A bipolar forceps according to claim 9, further comprising a knife assembly configured to cut tissue along the tissue seal when the wheel assembly is in a predetermined position relative to the jaw member.

14. A bipolar forceps according to claim 9, wherein the movable handle is movable between a closed position to cause the drive rod to move the wheel assembly distally relative to the jaw member and an open position to cause the drive rod to move the wheel assembly proximally relative to the jaw member.

15. A bipolar forceps according to claim 9, wherein the movable handle is movable between a closed position to cause the jaw member to move proximally relative to the wheel assembly and an open position to cause the jaw member to move distally relative to the wheel assembly.

* * * * *